United States Patent
Rad

(10) Patent No.: US 9,358,017 B2
(45) Date of Patent: Jun. 7, 2016

(54) SONOTRODE

(71) Applicant: Soring GmbH, Quickborn (DE)

(72) Inventor: Abtin Jamshidi Rad, Hamburg (DE)

(73) Assignee: Soring GmbH, Quickborn (DE)

( * ) Notice: Subject to any disclaimer, the term of this patent is extended or adjusted under 35 U.S.C. 154(b) by 529 days.

(21) Appl. No.: 13/743,432

(22) Filed: Jan. 17, 2013

(65) Prior Publication Data

US 2013/0184711 A1 Jul. 18, 2013

(30) Foreign Application Priority Data

Jan. 18, 2012 (DE) .......... 10 2012 200 666

(51) Int. Cl.
| | |
|---|---|
| A61B 17/32 | (2006.01) |
| A61B 17/16 | (2006.01) |
| H04R 31/00 | (2006.01) |
| B06B 3/00 | (2006.01) |

(52) U.S. Cl.
CPC ..... *A61B 17/1604* (2013.01); *A61B 17/320068* (2013.01); *B06B 3/00* (2013.01); *H04R 31/00* (2013.01); *A61B 2017/320096* (2013.01); *Y10T 29/49005* (2015.01)

(58) Field of Classification Search
CPC .......... A61B 17/1604; A61B 17/320068; A61B 17/1659; A61B 2017/320072; A61B 7/00
USPC .......... 606/167, 169–171, 176–178
See application file for complete search history.

(56) References Cited

U.S. PATENT DOCUMENTS

| | | | |
|---|---|---|---|
| 2001/0011176 A1 | 8/2001 | Boukhny | |
| 2003/0125620 A1 | 7/2003 | Satou et al. | |
| 2006/0004396 A1* | 1/2006 | Easley | A61B 17/1659 606/169 |
| 2006/0041220 A1 | 2/2006 | Boukhny et al. | |
| 2009/0236938 A1 | 9/2009 | Bromfield | |
| 2010/0030217 A1* | 2/2010 | Mitusina | A61B 17/32002 606/79 |
| 2010/0324581 A1 | 12/2010 | Mackool et al. | |

FOREIGN PATENT DOCUMENTS

GB WO2010049684 5/2010

* cited by examiner

*Primary Examiner* — Tuan V Nguyen
*Assistant Examiner* — Kevin Everage
(74) *Attorney, Agent, or Firm* — Alix, Yale & Ristas, LLP

(57) ABSTRACT

A sonotrode for an ultrasonic surgical instrument has a shaft and an instrument head at a distal end of the shaft. The instrument head is equipped with a cutting structure for the treatment of bones. The shaft has a helical cut-out. The helical cut-out is provided with a transversely running shoulder. A method produces a sonotrode and a surgical instrument having such a sonotrode. As a result of the shoulder in the helical cut-out, the torsional vibration of the instrument head is amplified such that bone material can be ablated in a particularly effective fashion.

19 Claims, 2 Drawing Sheets

SONOTRODE

BACKGROUND

The invention relates to a sonotrode for an ultrasonic surgical instrument having a shaft and an instrument head at the distal end of the shaft. The instrument head is equipped with a cutting structure for the treatment of bones. A helical cut-out is formed on the shaft. The invention moreover relates to a method for producing such a sonotrode.

By way of example, such sonotrodes can be used in dentistry to sever or ablate bone material of the patient. An ultrasound transducer creates a high-frequency mechanical vibration. The sonotrode is connected to the ultrasound transducer and is made to vibrate by the ultrasound transducer. When the cutting structure of the sonotrode is brought into contact with the bone, bone material is ablated by the high-frequency vibration.

It is known that a longitudinal vibration created by the ultrasound transducer can partly be converted into a torsional vibration of the instrument head by virtue of providing the shaft with helical cut-outs; in this respect see US2009/0236938A1, US2006/0041220A1, WO2010/049684A1. The shaft intrinsically twists as a result of the helical cut-outs when the longitudinal vibration from the ultrasound transducer acts on the proximal end of the shaft. As a result, the instrument head at the distal end of the shaft is excited to perform a torsional vibration.

In general, the amplitude of the torsional vibration increases the deeper and the wider the helical cut-outs cut into the material of the shaft. However, it is not possible to increase the amplitude of the torsional vibration arbitrarily in this fashion because the shaft must not be weakened too much by the cut-outs.

SUMMARY

A sonotrode and an associated production method achieve effective treatment of the bone.

The helical cut-out of the shaft is provided with a transversely running shoulder.

A few terms will initially be explained. A shoulder in the helical cut-out can be created by a region of the helical cut-out being cut deeper into the material of the shaft than in an adjacent region of the helical cut-out. The transition between the two regions is referred to as a shoulder.

The helical cut-out has a longitudinal extent that winds about the shaft. The shoulder is aligned transversely with respect to the longitudinal extent, i.e., includes an angle with the longitudinal extent. The shoulder can extend over the whole width of the helical cut-out. It is also feasible for the shoulder to extend only over part of the width of the helical cut-out.

A transversely running shoulder in the helical cut-out increases the amplitude of the torsional vibration at the distal end of the shaft. Thus, the instrument head at the distal end of the shaft is put into an intensive torsional vibration, allowing effective treatment of the bone material. The increased amplitude presumably is due to the fact that the shoulder forms a type of singularity for the force transmission within the shaft. There is an interruption in the force transmission which as a result yields an increased torsional vibration at the distal end of the shaft.

The shoulder can include an angle of 90° with the longitudinal extent of the helical cut-out. It was found to be particularly effective if the angle deviates from 90°. By way of example, the angle between the shoulder and the longitudinal extent of the helical cut-out can lie between 10° and 80°, preferably between 30° and 60°.

The shoulder can have an edge, which runs transversely to the helical cut-out. The edge can extend in a straight line over the whole width of the helical cut-out. However, trials have shown that it is advantageous for the effect according to the invention if the edge only extends in a straight line over a section of the width of the helical cut-out and is then interrupted. In this context, an interruption of the edge means that the edge does not continue in a straight line in the same direction. By virtue of the edge itself being interrupted again, there is a further break in the force transmission within the shaft, which has a positive effect on the amplitude of the vibration at the distal end of the shaft.

The amplitude of the vibration at the distal end of the shaft can be further increased if the helical cut-out has a plurality of shoulders with the aforementioned features. The shoulders can extend in parallel with respect to one another. The shoulders can include an angle of 90° with the longitudinal axis of the sonotrode.

The helical cut-out can be composed of a plurality of milled-out portions, with the shoulders being formed at the transition from one milled-out portion to the next milled-out portion. By way of example, a helical cut-out can comprise between eight and twelve milled-out portions. The milled-out portions can be aligned transversely to the longitudinal extent of the helical cut-outs.

By way of example, the milled-out portions can be created by a milling cutter initially piercing into the shaft and then being guided out of the material of the shaft again towards the side (i.e., perpendicular to the axis of the milling cutter and perpendicular to the axis of the sonotrode). Every milled-out portion then has a wall with a rounded contour at one end while it directly merges into the circumferential surface of the shaft at the other end. In order to interrupt the edge, the milling cutter can initially be moved a bit parallel to the longitudinal axis before the movement transversely to the longitudinal axis starts. An identical milled-out portion can naturally be achieved by an inverted sequence of movements of the milling cutter. So that a helical cut-out is created overall, the shaft can be displaced parallel to the longitudinal axis thereof and rotated about the longitudinal axis between one milled-out portion and the next milled-out portion, while the milling cutter keeps its initial position.

The sonotrode can have a plurality of helical cut-outs with the above-described features. The plurality of helical cut-outs is preferably arranged on the same longitudinal section of the shaft. The helical cut-outs can be interlaced with one another such that together they form a helical structure. By way of example, the helical cut-outs can extend over a length of between 8 mm and 15 mm of the shaft. In the circumferential direction, the helical cut-out can for example extend over an angle of 180°. Here the diameter of the shaft can for example lie between 5 mm and 8 mm. The angle between the longitudinal extent of the helical cut-out and the longitudinal axis of the sonotrode can lie between 30° and 60°.

From the proximal end to the distal end, the sonotrode can have a length of between e.g., 6 cm and 18 cm. The sonotrode can be embodied such that it extends in a straight line from the proximal end to the distal end.

The sonotrode is preferably matched to the ultrasound transducer of the associated ultrasonic surgical instrument such that a vibration node is formed in the central region of the sonotrode when the instrument with the sonotrode is operating. The helical cut-out is preferably arranged between the vibration node and the proximal end of the sonotrode. This means that, as seen from the proximal end, the helical cut-out is preferably arranged in the first half, more preferably in the first third, of the sonotrode.

The problem of the shaft being weakened when the helical cut-outs are cut too deep into the material of the shaft arises in particular if a channel extends through the interior, which channel can for example serve to supply a rinsing liquid to the distal end of the sonotrode. It follows that the advantages of the invention are particularly pronounced if a channel aligned parallel to the longitudinal axis of the sonotrode extends in the interior of the shaft. By way of example, the channel can have a diameter of between 0.5 mm and 1.5 mm, preferably of between 0.8 mm and 1.2 mm. The effect of the helical cut-out is that a force acting in the longitudinal direction at the proximal end of the sonotrode is partly converted into a torsional movement. It follows that the vibration of the instrument head at the distal end of the sonotrode is a superposition of a vibration in the longitudinal direction and a torsional vibration. It is advantageous for effective treatment of the bone if not only the torsional vibration but also the longitudinal vibration has a large amplitude. This can be achieved by virtue of the sonotrode being provided with a cross-sectional taper in the region between the helical cut-out and the instrument head.

The treatment of bone material can be further improved if further movement directions in addition to the longitudinal vibration and the torsional vibration are superposed in the instrument head. This can be achieved by virtue of the fact that the instrument head has an asymmetric shape with respect to the longitudinal axis of the sonotrode. As viewed from the proximal end, the instrument head then forms a type of unbalanced mass, which leads to the instrument head also carrying out a movement in the radial direction.

In order to avoid heat damage to the surrounding tissue, it is desirable for the splinters ablated from the bone to be removed from the operating field in a speedy fashion. If the splinters were to remain in the operating field, they would act as a type of heat store and increase the effect of the heat on the surrounding tissue. The removal of splinters is promoted by the instrument head undertaking a nodding motion. The instrument head then acts in the style of a shovel which removes the splinters. The instrument head can be induced to perform such a nodding motion by providing the distal end face of the sonotrode with a blind hole. By way of example, the diameter of the blind hole can be 0.2 mm to 0.3 mm. By way of example, the length of the blind hole can lie between 1.2 mm and 1.8 mm. The structure of the instrument head is weakened in a targeted fashion by means of the blind hole, and so the instrument head obtains the wanted intrinsic mobility. The feature of the blind hole has self-contained inventive content, even without the shaft being provided with a helical cut-out.

The blind hole can extend parallel to the longitudinal axis of the sonotrode and have a distance from the central axis of the sonotrode. The blind hole is preferably arranged in the region between the central axis and the cutting structure. In an advantageous embodiment, the end face is provided with two such blind holes. Moreover, the effect of such blind holes is that the vibration profile is optimized to the effect of reducing the feedback of forces from the instrument head to the ultrasound transducer and thereby preventing an overload of the ultrasound transducer.

A surgical instrument with an ultrasound transducer and a sonotrode is connected to the ultrasound transducer. The instrument can be provided with a feed line through which a liquid can be supplied to the channel in the interior of the shaft. Additionally, or as an alternative thereto, the feed line can be embodied such that a liquid is routed along the sonotrode on the outside.

A method for producing such a sonotrode is provided. In the method, a sonotrode semi-finished product comprises a shaft and an instrument head at the distal end of the shaft. A plurality of milled—out portions are created in the shaft. Respectively two milled-out portions are adjacent to one another such that a shoulder is formed at the transition between the milled-out portions. The adjacent cut-outs are respectively offset relative to one another both in the longitudinal direction of the sonotrode and in the circumferential direction such that the milled-out portions overall form a helical cut-out.

The milled-out portions can extend parallel to one another, with the greatest extent of the milled-out portion respectively including a right angle with the longitudinal axis of the sonotrode. In an advantageous embodiment the milling cutter initially pierces into the shaft in the radial direction and is then guided out of the material of the shaft in a lateral direction. The sequence of movement of the milling cutter can also be inverted. By way of example, the milling cutter can have a diameter of between 0.5 mm and 1.5 mm, preferably of between 0.8 mm and 1.2 mm. The greatest depth of the cut-out, i.e., the longest distance that the milling cutter penetrates into the material from the surface of the shaft, can for example lie between 0.5 mm and 1.5 mm, preferably between 0.8 mm and 1.2 mm.

The method can be developed with further features which were described above with reference to the sonotrode.

BRIEF DESCRIPTION OF THE DRAWINGS

In the following text, the invention will be described in exemplary fashion on the basis of an advantageous embodiment, with reference being made to the attached drawings. In detail.

DETAILED DESCRIPTION

Figure 1:
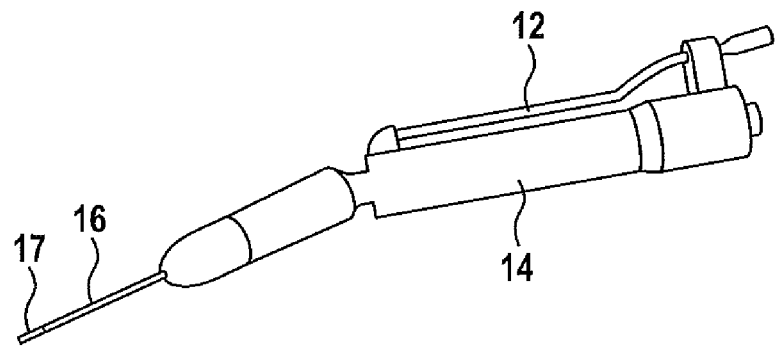
FIG. 1 shows a lateral view of an ultrasonic surgical instrument.
Figure 2:
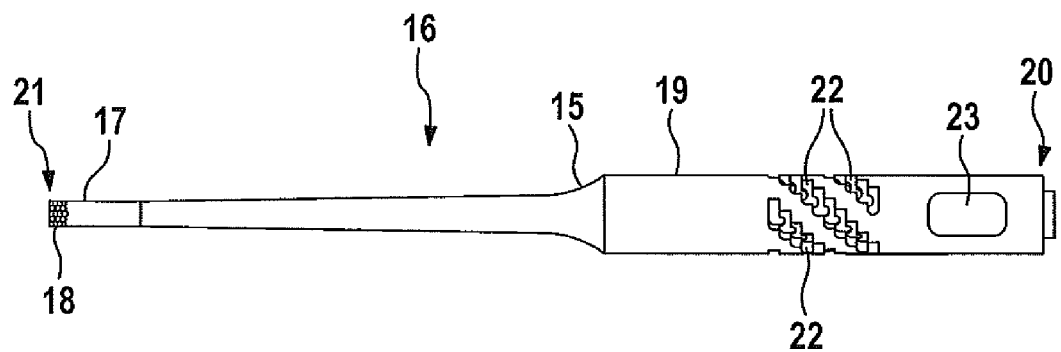
FIG. 2 shows a lateral view of a sonotrode.

An ultrasonic surgical instrument in FIG. 1 comprises a handle 14 at the rear end thereof, by means of which the surgeon can guide the instrument. Arranged in the interior of the instrument there is an ultrasound transducer (not visible in FIG. 1), which obtains an electrical AC voltage signal as input signal from a signal generator (likewise not illustrated in FIG. 1). By way of example, the AC voltage frequency can lie between 20 kHz and 40 kHz. The ultrasound transducer comprises a piezoelectric element by means of which the electrical signal is converted into a mechanical vibration which is aligned along the longitudinal direction of the instrument. The mechanical vibration is transferred to a sonotrode 16, which, as per FIG. 2, comprises a shaft 19 with an instrument head 17 at the distal end. The surface of the instrument head 17 illustrated towards the bottom of FIG. 1 and in the image plane of FIG. 2 is equipped with a cutting structure 18 and serves as a cutting surface. If the vibrating cutting structure 18 of the vibrating instrument head 17 is guided towards a bone, bone material is ablated.

The ultrasonic surgical instrument moreover comprises a line 12 (visible in FIG. 1) for being able to supply a rinsing liquid to the operating field. The rinsing liquid is routed to the instrument head 17 through a channel 24 arranged in the interior of the sonotrode 16 and there it can emerge into the operating field. The distal end of the channel 24 is visible in FIG. 4. Alternatively, the rinsing liquid can also be routed along the sonotrode on the outside.

As per FIG. 2, the sonotrode 16 extends in a straight line from a proximal end 20, by means of which the sonotrode 16 can be connected to the handpiece of the surgical instrument, to a distal end 21 on which the instrument head 17 is arranged. By means of a cross-sectional taper 15, the shaft 19 transitions from a thicker region near the proximal end 20 to a thinner region near the distal end 21. The shaft has a diameter of 6.5 mm in the thicker region. The sonotrode has a length of approximately 10 cm from the proximal end 20 to the distal end 21. At the proximal end 20 the shaft 19 is provided with recesses 23 which can be engaged by means of a spanner in order to screw the sonotrode 16 onto the handpiece or to release it from said handpiece.

When the sonotrode 16 is in operation and made to vibrate by the ultrasound transducer, a vibration node is formed approximately centrally between the proximal end 20 and the distal end 21. In the region between the vibration node and the proximal end 20, the shaft 19 is provided with a helical structure which comprises four interlaced helical cut-outs 22. Of the helical structure, which is illustrated in magnified fashion in FIG. 3, one helical cut-out 22 is visible substantially in its entirety and two helical cut-outs 22 are partly visible while the fourth cut-out is covered by the shaft 19 and therefore not visible.

The helical cut-outs 22 have a longitudinal extent by means of which they wind around the shaft 19. Along their longitudinal extent, the helical cut-outs 22 include an angle of 45° with the longitudinal axis of the shaft 19. The helical cut-outs 22 have a longitudinal extent of approximately 1.5 cm. The width perpendicular to the longitudinal extent, which cannot be determined unambiguously because the helical cut-outs 22 do not have a straight-lined edge, is of the order of 2 mm.

Every one of the helical cut-outs 22 is composed of ten milled-out portions 25, the greatest extent of which is respectively aligned perpendicular to the longitudinal axis of the shaft 19. The milled-out portions 25 are offset relative to one another both in the longitudinal direction and in the circumferential direction of the shaft 19 such that overall the helical shape is created.

The respectively first milled-out portion 25 of a helical cut-out 22 (respectively the right-hand cut-out 22 in FIG. 3) is created by virtue of a milling cutter piercing into the material of the shaft 19 in perpendicular fashion and the milling cutter then being guided to the side (upwards in FIG. 3) until it emerges from the material of the shaft 19.

The milling cutter can again be moved back into the initial position thereof in order to create the next milled-out portion 25. The shaft 19 is displaced relative to the milling cutter in the longitudinal direction and rotated slightly about its longitudinal axis such that the milling cutter can pierce into the 30 material of the shaft 19 in a new position in order to create the next milled-out portion 25. The displacement along the longitudinal direction is approximately half the width of the milled-out portion 25 such that there is an overlap with the first milled-out portion 25 when the milling cutter pierces into the material for the second milled-out portion 25. The milling cutter is then initially guided parallel to the longitudinal axis of the shaft 19 for a bit before it is guided out of the material with the movement in a lateral direction.

Figure 3:
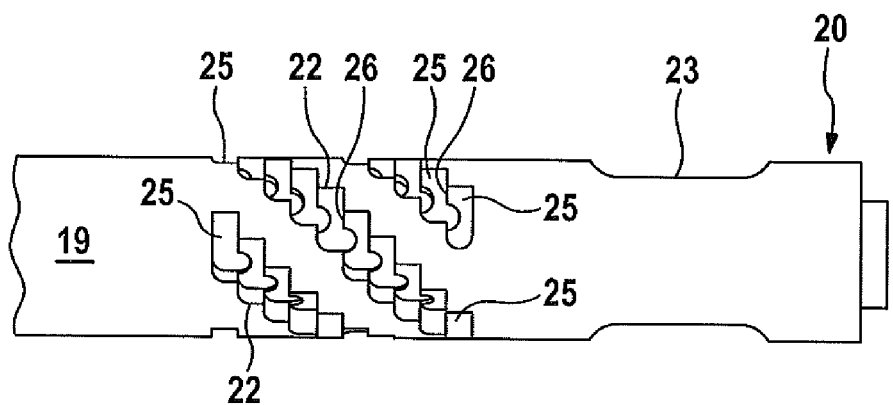
FIG. 3 shows a magnified illustration of a section from FIG. 2.

Since the milling cutter pierces into the shaft 19 from a different angular position in the second cut-out 22 compared to the first milled-out portion 25, an edge 26 is created between the milled-out portions 25. As a result of the milling cutter initially being guided in the longitudinal direction, the edge 26 between the first milled-out portion 25 and the second milled-out portion 25, which would otherwise have been a straight line, is interrupted. In FIG. 3 the interruption of the edge 26 is respectively shown as semicircular recess in the cut-outs 25.

A helical cut-out 22 is created by ten milled-out portions 25 adjacent to one another in this fashion. The edges 26 form shoulders within the meaning of the invention, which shoulders run transversely with respect to the helical cut-out 22. The described sequence during the creation of the helical cut-out 22 merely serves for explanatory purposes. Other sequences are also possible, for example by producing the milled-out portions 25 in a different sequence or the milling cutter moving in the opposite direction.

The longitudinal vibration, into which the proximal end 20 of the sonotrode 16 is excited by the ultrasound transducer, is partly converted into a torsional vibration by means of the helical cut-outs 22. The instrument head 17 at the distal end is thereby excited into a complicated movement which comprises torsional vibrations and longitudinal vibrations. As a result of the edges 26, which interrupt the helical cut-outs 22 in the transverse direction, the torsional vibration of the instrument head 17 has a greater amplitude than in the case of conventional helical cut-outs 22. The longitudinal amplitude is amplified by the cross-sectional taper 15.

Figure 4:
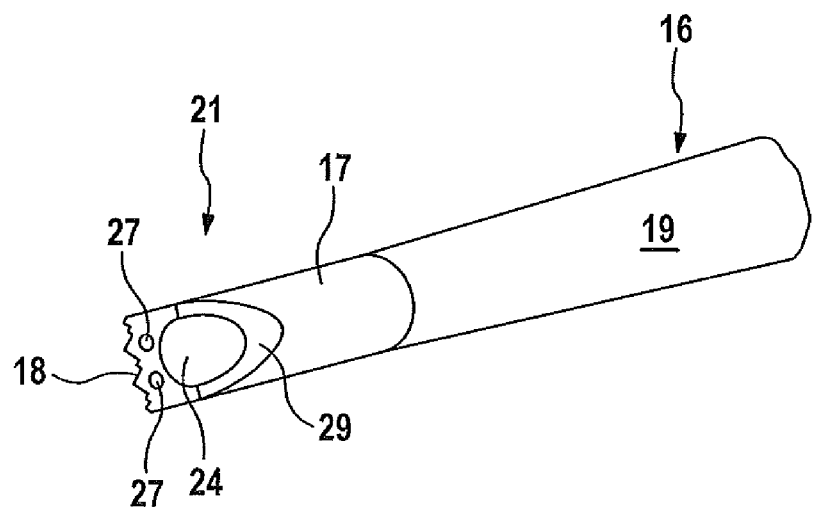
FIG. 4 shows a magnified illustration of a detail from FIG. 2 from a different perspective.

The distal end 21 of the sonotrode 16 is illustrated in a magnified fashion in FIG. 4, with the perspective being selected such that the end face with the outlet of the channel 24 is visible, while the cutting structure 18 points obliquely to the rear and is covered. The distal end face of the sonotrode 16 is provided with two blind holes 27, which extend parallel to the channel 24 and are arranged between the channel 24 and the cutting structure 18. The blind holes have a diameter of between 0.2 mm and 0.3 mm and a length of approximately 1.5 mm. As a result of the blind holes 27 and a chamfer 29, the instrument head 17 obtains an asymmetric shape with respect to the longitudinal axis of the sonotrode 16. This asymmetric shape leads to the instrument head 17 intrinsically carrying out a nodding motion. Splinters, which are ablated from the bone by the cutting structure 18, are removed in a particularly effective fashion as a result of the nodding motion.

The invention therefore presents a sonotrode in which the instrument head 17 carries out a multidimensional vibration by means of which the bone material can be ablated very effectively. Splinters detached from the bone material are removed well as a result of the additional nodding motion of the instrument head 17.

The invention claimed is:

1. A sonotrode for an ultrasonic surgical instrument having a shaft and an instrument head at a distal end of the shaft, the instrument head being equipped with a cutting structure for the treatment of bones and the shaft having a helical cut-out, characterized in that the helical cut-out has a longitudinal extent that winds about the shaft and the helical cut-out is provided with a transversely running shoulder with respect to the longitudinal extent of the helical cut-out wherein the helical cut-out has a first and second adjacent region, the first region is cut deeper into the material of the shaft than the second region and a transition between the two adjacent regions defines the shoulder.

2. The sonotrode according to claim 1, characterized in that the shoulder includes an angle of between 10° and 80° with the longitudinal extent of the helical cut-out.

3. The sonotrode according to claim 2, characterized in that the shoulder includes an angle of between 30° and 60° with the longitudinal extent of the helical cut-out.

4. A surgical instrument with an ultrasound transducer and a sonotrode connected to the ultrasound transducer, characterized in that the sonotrode is embodied according to claim 2.

5. The sonotrode according to claim 1, characterized in that the shoulder has an edge which runs transversely to the helical cut-out.

6. The sonotrode according to claim 5, characterized in that the edge extends in a straight line over a section of the helical cut-out and is then interrupted.

7. A surgical instrument with an ultrasound transducer and a sonotrode connected to the ultrasound transducer, characterized in that the sonotrode is embodied according to claim 6.

8. A surgical instrument with an ultrasound transducer and a sonotrode connected to the ultrasound transducer, characterized in that the sonotrode is embodied according to claim 5.

9. The sonotrode according to claim 1, characterized in that the helical cut-out has a plurality of shoulders.

10. A surgical instrument with an ultrasound transducer and a sonotrode connected to the ultrasound transducer, characterized in that the sonotrode is embodied according to claim 9.

11. The sonotrode according to claim 1, characterized in that the helical cut-out is composed of a plurality of milled-out portions.

12. A surgical instrument with an ultrasound transducer and a sonotrode connected to the ultrasound transducer, characterized in that the sonotrode is embodied according to claim 11.

13. The sonotrode according to claim 1, characterized in that the shaft has a plurality of helical cut-outs.

14. A surgical instrument with an ultrasound transducer and a sonotrode connected to the ultrasound transducer, characterized in that the sonotrode is embodied according to claim 13.

15. The sonotrode according to claim 1, characterized in that extending within the interior of the shaft there is a channel by means of which a liquid can be supplied to the distal end of the sonotrode.

16. The sonotrode according to claim 1, characterized in that a cross-sectional taper is provided between the helical cut-out and the instrument head.

17. The sonotrode according to claim 1, characterized in that the instrument head has an asymmetric shape with respect to the longitudinal axis of the sonotrode.

18. The sonotrode according to claim 1, characterized in that the distal end face of the sonotrode is provided with a blind hole.

19. A surgical instrument with an ultrasound transducer and a sonotrode connected to the ultrasound transducer, characterized in that the sonotrode is embodied according to claim 1.

* * * * *